United States Patent
Fauconet et al.

(10) Patent No.: US 9,796,651 B2
(45) Date of Patent: Oct. 24, 2017

(54) METHOD FOR CONTINUOUS PRODUCTION OF LIGHT ACRYLATES BY ESTERIFICATION OF A RAW ESTER-GRADE ACRYLIC ACID

(71) Applicant: Arkema France, Colombes (FR)

(72) Inventors: Michel Fauconet, Valmont (FR); Roger L. Roundy, Rosharon, TX (US); Stephane Denis, Leyviller (FR); Samuel M. Daniel, Malvern, PA (US)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 14/906,292

(22) PCT Filed: Jul. 24, 2014

(86) PCT No.: PCT/FR2014/051928
§ 371 (c)(1),
(2) Date: Jan. 20, 2016

(87) PCT Pub. No.: WO2015/015100
PCT Pub. Date: Feb. 5, 2015

(65) Prior Publication Data
US 2016/0159725 A1    Jun. 9, 2016

(30) Foreign Application Priority Data

Jul. 29, 2013 (FR) .................................. 13 57447

(51) Int. Cl.
| | |
|---|---|
| *C07C 67/08* | (2006.01) |
| *C07C 67/327* | (2006.01) |
| *C07C 51/09* | (2006.01) |
| *C07C 67/54* | (2006.01) |
| *C07C 67/62* | (2006.01) |

(52) U.S. Cl.
CPC .............. *C07C 67/08* (2013.01); *C07C 51/09* (2013.01); *C07C 67/327* (2013.01); *C07C 67/54* (2013.01); *C07C 67/62* (2013.01); *Y02P 20/582* (2015.11)

(58) Field of Classification Search
CPC ......... C07C 67/08; C07C 67/62; C07C 67/54; C07C 51/09; C07C 67/327
See application file for complete search history.

(56) References Cited

U.S. PATENT DOCUMENTS

| | | |
|---|---|---|
| 3,868,410 A | 2/1975 | Horlenko et al. |
| 5,187,309 A | 2/1993 | Esch et al. |
| 5,510,514 A * | 4/1996 | Fauconet ............... C07C 67/08 560/218 |
| 6,252,110 B1 | 6/2001 | Uemura et al. |
| 6,482,976 B1 | 11/2002 | Ho et al. |
| 6,605,738 B1 | 8/2003 | Ho et al. |
| 8,242,308 B2 | 8/2012 | Ho et al. |
| 8,530,700 B2 | 9/2013 | Ho et al. |
| 8,921,457 B2 | 12/2014 | Maruyama et al. |
| 2003/0204106 A1* | 10/2003 | Shibusawa ............. C07C 51/09 560/205 |
| 2004/0236143 A1 | 11/2004 | Martan et al. |
| 2007/0280866 A1 | 12/2007 | Balduf et al. |

FOREIGN PATENT DOCUMENTS

| | | | |
|---|---|---|---|
| CA | 2193407 | * | 6/1997 |
| CA | 2193407 A1 | | 6/1997 |
| FR | 1351243 A | | 1/1964 |
| WO | WO9852903 A1 | | 11/1998 |

* cited by examiner

*Primary Examiner* — Yate K Cutliff
(74) *Attorney, Agent, or Firm* — Lynn B. Morreale

(57) ABSTRACT

The present invention relates to methods by which the thermal dissociation of Michael adducts present in a stream of crude acrylic acid, called "crude ester grade", and the esterification reaction of acrylic acid present in the stream of crude acrylic acid, or generated in situ by thermal dissociation, with a light alcohol, are carried out simultaneously.

9 Claims, No Drawings

METHOD FOR CONTINUOUS PRODUCTION OF LIGHT ACRYLATES BY ESTERIFICATION OF A RAW ESTER-GRADE ACRYLIC ACID

CROSS-REFERENCE TO RELATED APPLICATIONS

This application is a national stage application under 35 U.S.C. §371 of PCT/FR2014/051928, filed Jul. 24, 2014, which claims benefit to FR patent application FR 13.57447, filed Jul. 29, 2013.

FIELD OF TECHNOLOGY

The present invention relates to the manufacture of light acrylates, and notably relates to a method for continuous preparation of light acrylates by direct esterification from a stream of crude acrylic acid and a light alcohol, in particular methanol or ethanol.

More particularly, the present invention relates to a method according to which the thermal dissociation of the Michael adducts present in a stream of crude acrylic acid, called hereinafter "crude ester grade", and the esterification reaction of the acrylic acid present in said stream of crude acrylic acid, or generated in situ by said thermal dissociation, with a light alcohol, are carried out simultaneously.

PRIOR ART AND THE TECHNICAL PROBLEM

Light acrylic esters (or light acrylates) are prepared from acrylic acid and light alcohol (such as methanol or ethanol) by simple esterification. The range of uses for the manufacture of polymers is extensive. Methyl acrylate (MA) is very often used in copolymerization processes for making fibres. Ethyl acrylate (EA) is used in particular in copolymerization processes for imparting cohesion to textile fibres.

Obtaining these monomers with a satisfactory degree of purity for the final industrial application is therefore essential and often challenging, and requires expensive purification techniques. Thus, to meet these purity requirements, quite particular attention is paid to the quality of the acrylic acid, which must be free from impurities that could generate by-products in the light acrylate. That is why the esterification reaction is generally carried out starting from a purified acrylic acid.

For synthesis of acrylic acid (AA), the most widely used industrial route is the oxidation of propylene. This synthesis of acrylic acid is called petrochemical synthesis and comprises two steps, the first is the oxidation of propylene to acrolein with simultaneous production of one molecule of water per molecule of acrolein and the second is the oxidation of acrolein to acrylic acid. This synthesis is generally carried out in two reactors using two catalytic systems specific to each of the oxidation steps, or in a single reactor having two separate catalyst beds.

Another route of synthesis of acrylic acid uses glycerol or glycerin as raw material, which is submitted firstly to dehydration leading to acrolein with simultaneous production of 2 molecules of water per molecule of acrolein, the latter then being submitted to oxidation to form acrylic acid. This route also comprises two steps with, as a point in common, the presence of acrolein as intermediate. It is in the course of industrial development as it is a "green" process using a renewable natural raw material and not a fossil material such as propylene.

The effluent leaving the reactor after the oxidation of acrolein to acrylic acid contains, besides the reaction products, acrylic acid and water, a whole range of by-products constituting impurities, both by the propylene route and by the glycerol route. These by-products are notably:

light compounds that are incondensable in the conditions of temperature and pressure usually employed (nitrogen, oxygen, residual reactant, carbon monoxide and dioxide formed in small amounts by final oxidation);

condensable light compounds: in particular water, unconverted acrolein, light aldehydes, such as formaldehyde, acetaldehyde and acetic acid, the main impurity generated in the reaction section;

heavy compounds: notably furfuraldehyde, benzaldehyde, maleic anhydride, benzoic acid.

In the acrylic acid synthesis process, the effluent leaving the reactor, regardless of the route chosen, is submitted to a chain of treatment and purification that can be summarized as follows:

Acrylic acid is recovered from the gas mixture resulting from the 2nd step, by introducing this gas at the bottom of an absorption column, where it meets, in counter-current, a solvent introduced at the top of the column. In most of the processes described, the solvent used in this column is water or a high-boiling hydrophobic solvent. By removing the incondensables, this step allows "crude" acrylic acid to be formed.

In the case of absorption processes using water as absorbent solvent, the additional purification steps comprise a dehydration step, generally carried out in the presence of a non-water-miscible solvent, in an extraction column or a heteroazeotropic distillation column, then a step of removal of the light compounds, in particular acetic acid and formic acid, this step generally being called "topping". Finally, a step of separation of the heavy compounds is carried out by distillation, this step generally being called "tailing" and leading to an "industrial" acrylic acid. In the case of processes using a hydrophobic solvent, the steps are essentially the same, except for the removal of water, which is effected at the top of the first absorption column.

Recently, novel "solvent-free" technologies for recovery/purification of acrylic acid have appeared, involving a reduced number of purification stages and eliminating the introduction of external organic solvent. Patent EP 2 066 613 describes a process for the recovery of acrylic acid without using azeotropic solvent and while employing only two columns for purification of the cold gaseous reaction mixture: a) a dehydration column, where the gas stream distilled at the top is condensed and sent to the dehydration column in the form of reflux in order to absorb the acrylic acid, and b) a finishing column fed with the bottom stream from the first column, in which, i) the residual water and the residual acetic acid are distilled at the top and recycled at the bottom of the first column, ii) a stream comprising the heavy by-products and acrylic acid is removed at the bottom, in order to optionally be used in the production of acrylic esters, and iii) a stream of acrylic acid of industrial grade is recovered by side withdrawal in the liquid or vapour form.

During these various steps of treatment/purification, covalent side reactions of Michael addition on the double bond of the acrylic acid, generating compounds corresponding to the general term Michael adducts, may take place.

Essentially these are oligomers of acrylic acid, principally composed of Michael adduct molecules known as acrylic acid dimer (3-acryloxypropionic acid, n=1) and acrylic acid trimer (3-(3-acryloxypropionylpropionic acid, n=2). They are characterized by a boiling point above the boiling point of the products employed in the reaction, and will be found in the heavy compounds fraction separated during the final step of tailing.

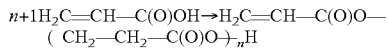

Other Michael adducts can also coexist with the derivatives from the addition of acrylic acid to itself, which involve the nucleophilic addition of compounds present in the medium for purification of the acrylic acid, such as, for example, water, to the double bond of the acrylic acid or acrylic acid oligomers:

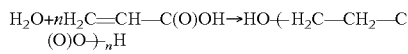

The process of treatment/purification of acrylic acid therefore leads to obtaining, on the one hand, a stream of purified acrylic acid generally designated as being of "industrial" grade, used notably as raw material for producing light acrylates, and on the other hand a stream comprising heavy compounds, notably including large amounts of oligomers of acrylic acid.

In the conventional process, the heavy fraction is removed, but most often, in order to avoid loss of products that can be upgraded, it is submitted to a high-temperature thermal treatment, in the presence or absence of a catalyst, for dissociating the oligomers and recovering the acrylic acid monomer, the final residue then being removed and the recovered acrylic acid being recycled as raw material to an esterification process (EP 887 334; FR 1 351 243). The drawbacks of this type of treatment are the high viscosity of the residue, which can no longer be conveyed in the pipelines, and fouling of the wall of the cracking reactor.

Moreover, the production of acrylic esters comprising the esterification reaction of industrial acrylic acid with an alcohol, followed by a purification treatment, is also accompanied by the formation of Michael adducts: these are principally acrylic acid oligomers and derivatives resulting from their esterification with alcohol used for the esterification reaction, and also products of Michael addition of the alcohol to the double bonds of the compounds mentioned:

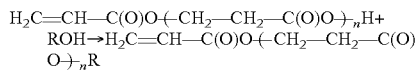

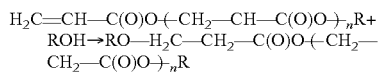

In document U.S. Pat. No. 3,868,410, these Michael adducts are advantageously converted to monomers by thermal treatment at a temperature above 180° C., with a view to recycling them to the esterification step.

In order to improve the yield in recovery of valuable products generated by thermal cracking of the heavy fractions formed, on the one hand during the synthesis of acrylic acid, and on the other hand during the synthesis of acrylic esters, it was proposed, in document EP 2 727 964, to conduct thermal dissociation on a mixture of these heavy fractions, in the absence of catalyst, which has the effect of reducing fouling in the dissociation reactor as well as lowering the viscosity of the residue obtained at the end of the operation of thermal dissociation.

In addition to the fact that the abovementioned methods do not resolve the problems inherent in the formation of Michael adducts during the steps of synthesis and/or purification of acrylic acid and/or of acrylic esters, such as:
the use of large amounts of polymerization inhibitors for limiting the radical polymerization reactions;
complexity of the steps of separation of the heavy fractions;
high cost of thermal cracking of the heavy fractions for recovering the valuable compounds;
difficulty of removing the heavy residues after cracking and fouling of the cracking reactor;
the processes for esterification of acrylic acid have drawbacks which result directly from the use of a purified grade of acrylic acid as raw material for producing the acrylic esters.

To reduce these drawbacks, the method of production of light acrylates described in document WO 91/01966 uses an aqueous solution of crude acrylic acid as raw material for the esterification reaction. The aqueous solution is received from the column for absorption of the gas mixture from oxidation of acrolein in the process for producing acrylic acid, and it comprises from 50% to 70% of acrylic acid and the impurities inherent in its production. In the method in WO 91/01966, the aqueous solution of crude acrylic acid is not purified in a specific purification plant, before being fed into the esterification reactor; it is introduced directly at the bottom of the distillation column used for separating the products from the esterification reactor, to result in a stream enriched in acrylic acid at the bottom of said column, which is recycled to the esterification reactor. This method is not, however, economic on an industrial scale.

Document WO 00/78702 describes a method of synthesis of acrylic esters, in particular of butyl acrylate, in which the esterification reaction is carried out at a temperature and a pressure sufficient to permit cracking of the Michael adducts formed in situ or introduced into the reactor, in one and the same reaction zone, and to vaporize the ester produced. Typically, the reaction is carried out at a temperature in the range from 100 to 160° C., and at a pressure in the range from 0.01 to 100 bar. This method allows acrylic acid of low purity to be used, notably acrylic acid comprising acetic acid and/or dimer and/or other Michael adducts at a content above 0.5%.

In document US 2004/0236143, the process for producing acrylic esters can start from a crude grade of acrylic acid, i.e. comprising acetic acid, aldehydes, heavy compounds such as maleic anhydride, this crude grade of acrylic acid optionally being pretreated by means of an amine compound to reduce its content of carbonylated compounds, and whose content of dimers is of the order of 0.01-5%. The purification steps result in obtaining a methyl acrylate with a purity above 99.9%.

In the documents WO 98/52903 and WO 98/52904, provision has been made to produce butyl acrylate by direct esterification in two reactors placed in series operating at two different temperatures, the temperature of the second reactor being higher, so as to continue the esterification reaction and to thermally dissociate the heavy products. The first reactor is fed with pure reactants (butanol and acrylic acid) and with a recycled stream of heavy products, in particular a fraction of heavy esters which is separated during the purification of the butyl acrylate. This method requires the use of two reactors and uses pure acrylic acid as raw material.

The document US 2007/280866 describes the thermal dissociation of acrylic acid oligomers in the presence of a cleaving reactant, such as butanol. The dissociation is carried out batchwise. The conditions of the reaction are not suitable for the implementation of an industrial production method continuously.

The problem to be solved by the present invention consists of developing a method for manufacturing light acrylic esters that does not have the drawbacks of the existing methods, and permits the continuous preparation of methyl acrylate or ethyl acrylate of high purity, from a crude grade of acrylic acid having a high content of Michael adducts, designated hereafter in the description of the invention as being "of crude ester grade". The target objective is also to achieve a high esterification yield for all of the upgradeable acrylic acid present in the acrylic acid of the crude ester grade, without having recourse to a specific device for cracking said adducts.

This aim is achieved according to the present invention by carrying out, simultaneously in a single reactor, the thermal dissociation of the Michael adducts present in a stream of crude acrylic acid and the reaction of esterification of the acrylic acid present in the stream of crude acrylic acid and/or generated in situ by said thermal dissociation, the effluent leaving the reactor then being submitted to a chain of treatment and purification leading to recovery of methyl acrylate or of ethyl acrylate of high purity.

One of the aims of the present invention is thus to upgrade, in an esterification process, all of the valuable products potentially recoverable from a heavy fraction generated in an acrylic acid synthesis process. Another aim of the present invention is to reduce the overall amounts of final residue to be incinerated in processes for production of acrylic acid and/or acrylic esters, under conditions which make it possible to obtain the final residue with a viscosity acceptable for facilitating its removal.

According to the method of the invention, the Michael adducts generated during the esterification reaction, such as oligomers of acrylic acid or of acrylate, can be dissociated thermally within the reactor as they are formed, thus optimizing plant productivity.

The method according to the invention therefore only requires a moderate number of steps in a simplified apparatus, and produces light acrylates of high purity with a final residue that is sufficiently fluid to be removed easily.

SUMMARY OF THE INVENTION

The invention relates firstly to a method for continuous preparation of light acrylate, by reaction of a light alcohol with a stream of acrylic acid of crude ester grade comprising Michael adducts at a content by weight above 8%, according to which the following are carried out simultaneously, in a single reaction zone: the thermal dissociation of the Michael adducts present in said stream of acrylic acid of crude ester grade, or generated in situ in the reaction zone, and the reaction of esterification, with a light alcohol, of the acrylic acid present in said stream of acrylic acid of crude ester grade and/or generated in situ by said thermal dissociation, the effluent leaving the reaction zone then being submitted to a chain of treatment and purification leading to obtaining a purified light acrylate, the reaction residue remaining sufficiently fluid to be withdrawn using a pump.

According to the invention, the light acrylate is selected from methyl acrylate and ethyl acrylate, and the corresponding light alcohol is selected from methanol and ethanol. Preferably, the light acrylate is methyl acrylate.

More precisely, the invention relates to a method for continuous preparation of light acrylate selected from methyl acrylate and ethyl acrylate by reaction of the corresponding light alcohol selected from methanol and ethanol with a stream of acrylic acid of crude ester grade, in the presence of at least one acid catalyst and of at least one polymerization inhibitor, in a reaction zone comprising a reactor connected to a distillation unit, characterized in that:

the stream of acrylic acid of crude ester grade comprises oligomers of acrylic acid at a content by weight above 8%;

the molar ratio of alcohol to acrylic acid contained in the form of monomer, dimer or trimer in the stream of acrylic acid of crude ester grade is between 1.2 and 1.5;

the reactor temperature is above 130° C.;

the concentration by weight of acid catalyst is maintained above 2.5% in the reaction mixture;

the concentration of polymerization inhibitor in the reactor is adjusted to a value above 50 ppm;

the effluent leaving the distillation unit is submitted to a chain of treatment and purification leading to obtaining a purified light acrylate;

a residence time of the reaction residue in the reactor longer than 50 hours is maintained.

The method of the invention is particularly suitable for optimizing the productivity and the economics of a method of manufacture of light acrylates.

According to one embodiment of the invention, the stream of acrylic acid of crude ester grade is derived from a production process using propylene or propane as raw material.

According to one embodiment of the invention, the stream of acrylic acid of crude ester grade is derived from a production process using glycerol or glycerin as raw material.

According to one embodiment, the stream of acrylic acid of crude ester grade results from a process for the dehydration of lactic acid or ammonium lactate to give acrylic acid or from a process for the dehydration of 3-hydroxy-propionic acid or of its ammonium salt to give acrylic acid.

DETAILED DESCRIPTION OF THE INVENTION

The invention will now be described in more detail and non-exhaustively in the description given hereunder.

In that which follows, the "upgradeable acrylic acid" is composed of the acrylic acid monomer and of the Michael addition derivatives inherent to the synthesis of acrylic acid, in particular acrylic acid oligomers, which are present in the acrylic acid of crude ester grade.

In that which follows, the expressions "thermal dissociation" and "thermal cracking" have the same meaning; the expression "between" or "in the range from" is to be interpreted with limits included.

Reaction residue is understood to mean the fraction enriched in heavy by-products which do not react, accumulated in the reactor, which it is necessary to periodically purge from the reactor.

Unless otherwise indicated, the concentrations described in the description of the invention are concentrations by weight.

Stream of Acrylic Acid of Crude Ester Grade

The method by which the stream of acrylic acid of crude ester grade was obtained is of no importance for the method according to the invention, provided it is a stream of acrylic acid having a high content of Michael adducts, notably a content by weight of oligomers of acrylic acid above 8%, in particular a content of dimers of acrylic acid above 8%, preferably in the range from 8% to 25%, and a content of trimers of acrylic acid above 0.1%, preferably in the range from 0.5 to 3%.

The stream of acrylic acid of crude ester grade generally has a content of upgradeable acrylic acid above 90%.

The stream of acrylic acid of crude ester grade can in addition contain high-boiling heavy by-products, inherent in the synthesis of acrylic acid, such as furfuraldehyde, maleic anhydride, benzaldehyde or benzoic acid, and polymerization inhibitors.

The content by weight of heavy compounds can typically be:
Furfuraldehyde: 0.03-0.5%
Maleic anhydride: 0.3-4%
Benzaldehyde: 0.05-0.5%
Benzoic acid: 0.2-1%

According to one embodiment, the acrylic acid of crude ester grade can be obtained during purification of crude acrylic acid recovered by means of an absorption column fed with a solvent, such as water or a hydrophobic solvent, at the outlet of the acrylic acid synthesis reactor.

This purification can notably comprise a first dehydration step, generally carried out in the presence of a non-water-miscible solvent, in an extraction column or heteroazeotropic distillation column, followed by a step of removal of the light compounds, in particular acetic acid and formic acid, said step generally being called "topping". Finally, a final step of tailing performed by distillation separates the heavy fraction comprising high-boiling by-products and Michael adducts, which can be used as acrylic acid of crude ester grade.

Alternatively, the acrylic acid of crude ester grade can be obtained during purification of acrylic acid recovered by means of a dehydration column without using solvent for extraction or azeotropic distillation, at the outlet of the acrylic acid synthesis reactor, as described in patent EP 2 066 613. In this type of process, the acrylic acid contained in the gas from the reaction section is absorbed in a first column in counter-current with an essentially aqueous liquid stream from the reaction gas, partially condensed and refluxed to the top of the column. The concentrated stream of acrylic acid recovered at the bottom of the column is purified in a second column, which carries out additional topping (removal of light top residues recycled in the first column) and tailing (recovery of acrylic acid of crude ester grade at the bottom), the purified acrylic acid of industrial grade being withdrawn as a sidestream. The purification steps are approximately equivalent to those of the process using adsorption in water and then an azeotropic solvent, the step of topping of the light products being carried out in the first column at the same time as the dehydration step, and the final step of separation of the heavy compounds being carried out in the second column.

According to one embodiment, the acrylic acid of crude ester grade comprises, or consists of, the heavy fraction separated at the bottom of the last purification step called tailing in an acrylic acid synthesis process.

According to one embodiment, said stream of acrylic acid of crude ester grade partly comprises the stream separated at the bottom of the tailing step in an acrylic acid synthesis process.

The operating conditions of the method according to the invention are adapted so as to dissociate, almost quantitatively, the Michael addition derivatives and oligomers present in said stream of acrylic acid of crude ester grade to regenerate the acrylic acid monomer, and carry out the esterification reaction. According to the invention, an acrylic ester is obtained at a yield above 95%, expressed as molar percentage of ester manufactured relative to the upgradeable acrylic acid contained in the acrylic acid of ester grade, essentially introduced in the form of monomer, dimer or trimer $$Yield = \frac{\frac{m_{ester}}{MM_{ester}}}{\frac{(m_{AAmonomer} + m_{AAdimer} + m_{AAtrimer})}{72}}$$

where $m_x$=mass of species x and $MM_x$=molar mass of species X

Section for Reaction and Recovery of the Crude Acrylic Ester

The reaction zone, generally comprising an esterification reactor connected to a distillation unit, is fed continuously with the stream of acrylic acid of crude ester grade, a light alcohol (methanol or ethanol), and an esterification catalyst. The average feed flow rate of the reactants is generally between 0.1 and 0.5 T/h per $m^3$ of useful volume of the reactor, preferably between 0.2 and 0.3 T/h per $m^3$ of useful volume of the reactor.

The esterification reaction is carried out in the presence of a molar excess of alcohol relative to the acrylic acid present in the form of monomer, dimer and trimer.

The molar ratio of alcohol to acrylic acid present in the form of monomer or of oligomer is generally between 1.2 and 1.5, preferably between 1.3 and 1.45. The alcohol is fed into the reactor, alone or mixed with other reactants or recycled streams, preferably directly in the liquid phase consisting of the efficiently stirred reaction mixture, or through static or dynamic distribution systems, for example upstream of a pump, permitting dispersion of the reactant in the form of fine droplets. The known systems of mixers permitting rapid mixing of 2 liquids or rapid dispersion of a gas in a liquid can be used.

The so-called esterification reaction is carried out in the reactor at a high temperature so as to provide simultaneous dissociation of the Michael adducts, generally at a temperature above 130° C., preferably in the range from 135° C. to 155° C., or from 140° C. to 145° C., generally at a pressure from 0.9 to 1.3 bar.

A strong mineral acid, such as sulphuric acid or phosphoric acid, or an organic acid, such as methanesulphonic acid (MSA), para-toluenesulphonic acid, benzenesulphonic acid, dodecylbenzenesulphonic acid, xylenesulphonic acid, or mixtures thereof, is generally used as esterification catalyst. Methanesulphonic acid is preferably used as the esterification catalyst.

The catalyst is advantageously introduced continuously in order to maintain a concentration in the reactor above 2.5%, preferably in the range from 3% to 5% relative to the reaction mixture.

To limit the formation of polymers during the reaction, polymerization inhibitor(s) is (or are) introduced at the same time as the reactant feed stream. Examples of polymerization inhibitors that can be used are phenothiazine, or a derivative of phenothiazine, amine derivatives such as diphenylamine, or diphenylene-amine, phenolic compounds such as hydroquinone, hydroquinone monomethyl ether, di-tert-butyl para-cresol (BHT), or di-tert-butylcatechol, or N-oxyl compounds such as TEMPO (2,2,6,6-tetramethyl-1-piperidinyloxy) or TEMPO derivatives, such as 4-hydroxy-TEMPO, manganese salts, or copper compounds such as copper carbamates, alone or mixtures thereof in all proportions.

Preferably, phenothiazine or a mixture of phenothiazine and hydroquinone is used as polymerization inhibitor.

The polymerization inhibitor can be introduced in the reactor and/or at the top of the distillation unit in the reaction zone.

The polymerization inhibitor is introduced in the reaction zone in such a way that the concentration of polymerization inhibitor in the reactor is maintained at a value above 50 ppm, preferably above 100 ppm, more preferably at a value between 300 ppm and 1000 ppm. The concentration of inhibitor can be monitored by analysis, for example by liquid chromatography.

This level of concentration makes it possible, on the one hand, to eliminate any loss of efficiency of the polymerization inhibitor, on the other hand, to maintain an adequate efficiency of the catalyst, due to its possible reactions with the acid catalyst, and furthermore to reduce the viscosity of the final reaction residue in the reactor.

It may be advantageous to add phenothiazine as polymerization inhibitor at different points of the reaction zone, for example in the reactor, in the distillation unit, and at the top reflux of the distillation unit.

It may be advantageous to introduce an oxygen-containing gas in the reaction zone, especially when the polymerization inhibitor contains a phenolic compound.

The reaction is carried out in the reactor for a time such that the recovery of products that can be upgraded generated by thermal dissociation and the yield in esterification are very high, and such that there is a very small amount of reaction residue to be removed.

This corresponds to a residence time of the reaction residue in the reactor longer than 50 hours, preferably longer than 100 hours, the residence time being expressed as the average time during which the reaction residue is held in the reactor before being purged, calculated from the ratio of the volume of reaction mixture to the purge rate. In the reaction conditions, the reaction residue, enriched with heavy products coming essentially from the reaction stream of acrylic acid, remains sufficiently fluid to be withdrawn using a pump and to be able to be sent to a thermal oxidizer for removal and optional recovery of energy, or to any other appliance for the purpose of final upgrading.

Preferably, the dynamic viscosity of the residue measured at 100° C. should be less than 200 cP, measured with a viscosimeter, such as, for example, a Brookfield rotary viscosimeter. It may be advantageous to add a viscosity depressant, for example methanol or acetic acid, at a content in the range from 10 to 30%, to facilitate the subsequent pumping operations after storage or transport at lower temperature for its removal or recycling as heat-transfer fluid, for example.

Advantageously, the reaction residue is taken at the temperature of the esterification reaction permitting thermal dissociation of the Michael adducts and it is sent to storage, maintained at a temperature near the reaction temperature to within 10° C. The gases vented from the storage tank are collected and recycled to the reactor, thus permitting additional recovery of acrylic ester from the residue during this storage phase before removal.

The stages of reaction (esterification and cracking) and recovery (removal and purification of the reaction products) are closely related. The reaction conditions control the composition of the reaction mixture in the reactor, which conditions the formation of light acrylate/water and light acrylate/light alcohol azeotropic mixtures. These mixtures are purified in the distillation unit and also depend on the composition of the reflux imposed at the top of said unit. In return, the mixtures formed have a significant impact on the effectiveness of the expected reaction.

For example, during the esterification of acrylic acid by methanol to produce methyl acrylate, a first methyl acrylate/methanol azeotropic mixture relatively rich in methanol (52% in theory) coexists with a second methyl acrylate/water azeotropic mixture. The first azeotropic mixture has a negative impact on the progression of the reaction by favouring the removal of a reactant (the alcohol) from the reaction mixture. The second azeotropic mixture has a positive effect since it makes it possible to displace the esterification equilibrium but its removal is put at a disadvantage relative to the first mixture due to a boiling point greater by 9° C. and as a result of its relative dearth in water (9% in theory).

Consequently, the reaction conditions tending to favour the formation of the second azeotropic mixture (methyl acrylate/water) rather than the first (methyl acrylate/methanol) make it possible to improve the yield of the reaction.

They are carried out in a reaction zone comprising a reactor and a distillation unit permitting the simultaneous removal of the water produced by the esterification reaction, of the ester manufactured, of the excess unreacted alcohol and also of small amounts of residual impurities or impurities generated by the reaction, in order to form a mixture referred to as crude ester.

The reaction zone can be a reactor, the gas phase of which is connected to a distillation column, or a reactive column consisting, in the bottom part, of a reaction section containing the liquid reaction mixture and, in the top part, of a distillation section.

The reactor can be any type of stirred reactor known to a person skilled in the art. Preferably, the reactor or the reaction section of the reactive column are fed continuously with the mixture of reactants, a portion of the reaction mixture is withdrawn and reheated in an external exchanger and the reheated stream is recycled to the reactor using a pump.

Preferably, the reactor, the exchanger, the pump, the transfer lines and any equipment in contact with the reaction mixture are made of a corrosion-resistant material or are coated with corrosion-resistant materials.

The distillation column or the distillation section of the reactive column can be composed of plates and/or random packings and/or stacked packings of any type available for the rectification of mixtures and suitable for the distillation of polymerizable compounds. It is equipped with a condenser and with a liquid feed at the top, which provides a liquid reflux in the column.

The number of plates and/or the height and the type of packing of the column are chosen so as to limit the entrainment of unreacted acrylic acid in the effluent recovered at the column top.

Optionally, downstream of the condenser, a decanter can be installed in order to separate an organic phase comprising most of the ester and traces of water and of unreacted alcohol, and an aqueous phase comprising most of the water generated by the reaction and of the unreacted alcohol, and also small amounts of ester.

The removal of the water generated by the esterification is carried out essentially by entrainment in the form of an azeotropic mixture with the light ester manufactured. In order to limit the entrainment of the unconverted light alcohol by the azeotropic mixture with the ester manufactured, which would have the consequence of a reduction in the reaction yield, an excess of ester is maintained, so as to promote the esterification reaction by removal of the water formed. This is carried out by virtue of a reflux of an essentially water-free light acrylate phase which, expressed as flow rate by mass relative to the flow rate by mass of the feed of reactants to the reaction zone, is kept above 0.8, preferably between 1 and 2.5, indeed even between 1 and 1.2.

Said water-free refluxed light acrylate, preferably containing less than 5% by weight of water, may come from a portion of the organic phase separated in the decanter and/or from a fraction separated during purification of the distilled effluent, for example at the bottom of a distillation column for light compounds or at the bottom of a column for separation of heavy compounds and thus makes it possible to recycle the light acrylate present in these fractions.

The distilled effluent comprising the crude ester mixture is submitted, either after decanting or directly, to a chain of treatment and purification leading to obtaining a purified light acrylate.

According to the method of the invention, the light acrylate present in the crude ester mixture is produced at a yield above 95%, generally in the range from 95% to 98%, expressed in number of moles of light acrylate produced relative to the number of moles of acrylic acid introduced in the form of acrylic acid monomer, dimer or trimer.

Purification Section

Each of the phases (organic and aqueous) obtained by decanting the crude ester is subjected to a purification treatment, targeted at recovering the purified ester essentially present in the organic phase by removal of water and the impurities present at a low concentration and by recovering the alcohol which is found therein, and in recovering, for recycling purposes, the alcohol and the low concentrations of ester which are present in the aqueous phase.

Advantageously, this is carried out in a liquid/liquid extraction stage applied to the crude ester mixture after decanting, so as to increase the concentration of alcohol in the aqueous phase and to reduce this concentration in the organic phase, and thus to improve the recovery of the alcohol for the purposes of recycling to the reaction stage.

The extraction column is fed at the bottom with the organic phase resulting from the decanting and at the top with the aqueous stream recovered at the bottom of the column for recovery of light alcohol.

The aqueous phase obtained at the bottom of the extraction column, enriched in alcohol, is advantageously partially sent to a distillation column for recovering, at the top, the light alcohol, which is then recycled to the reaction, and, at the bottom, an aqueous phase depleted of light alcohol that can be used as extraction solvent fed into the top of the extraction column. A portion of this aqueous phase is removed.

Alternatively, the crude ester effluent distilled from the reaction zone may be sent directly to the extraction column, without preliminary separation in a decanter, thus minimizing the equipment necessary for treatment of the distilled effluent, and facilitating control of the operations of separation and recycling of the residual alcohol and/or of the scrubbing water.

The scrubbed organic phase is thus essentially free from light alcohol and comprises the light acrylate required, but still contains light by-products and heavy by-products as impurities.

The scrubbed organic phase is sent to a first distillation column for removing the light by-products that the light acrylate contains, notably including traces of alcohol, acetates, dimethyl ether or diethyl ether; the latter are withdrawn from the top of said column, partly to be recycled to the reaction zone or to the extraction step, and partly removed.

At the bottom of said distillation column, the light acrylate is recovered, still comprising heavy impurities including notably methyl or ethyl alkoxypropionate, small amounts of methyl or ethyl acryloxypropionates, dimethyl or diethyl maleate and methyl or ethyl benzoate and polymerization inhibitors.

This stream is sent to a separating column for final purification. At the bottom of the separation column, a light acrylate with high concentration of heavy impurities is recovered, which is partly removed, partly recycled as reflux to the distillation unit in the reaction zone.

At the top of the separation column, a light acrylate is recovered with purity above 99%.

The advantages of the invention are now illustrated without implied limitation in the following examples.

EXAMPLES

Example 1

The experimental set up is composed of a stirred reactor with a useful volume of 1 liter heated by recirculation in its jacket of hot oil at regulated temperature, surmounted by a distillation column. The reactor is equipped with an inlet for the feeding, via a pump, of the mixture of reactants, with a separate feed of 70% MSA catalyst in water via a second pump, with a temperature measurement in the liquid and with a withdrawal point at the bottom. The column is equipped with 7 perforated plates comprising weirs, with an inlet at the column top for feeding the reflux via a third pump, with a vertical condenser placed over the exiting gas phase at the column top, fed via a fourth pump with a water mixture comprising 2% hydroquinone, with an intermediate tank equipped with a level control and with a receiving tank/decanter withdrawing, using a fifth pump, the crude mixture of distilled ester.

In a first phase lasting 3 weeks during which the operating conditions and the composition of the mixture change, the residue mixture rich in heavy compounds is formed by gradual enriching of the reaction mixture, in order to finally achieve the conditions which make it possible to simultaneously carry out the esterification of the acrylic acid and the thermal cracking of the oligomers present in the reactive acrylic acid and generated during this operation.

On conclusion of this first enriching phase, the operating conditions and compositions are stabilized; the MSA concentration measured in the reaction mixture is 4.5%.

A feed mixture, consisting of 57.9% of acrylic acid of crude ester grade, of 32.4% of methanol, and of 7.6% of methyl acrylate and of 2.1% of water (these 2 compounds resulting from the recycling of the stream originating from subsequent stages) is fed to the reactor with a flow rate of 300 g/h. The acrylic acid of crude ester quality is composed of 84.4% of acrylic acid, 12.8% of acrylic acid dimer and 0.6% of acrylic acid trimer, 0.5% of phenothiazine, 0.3% of hydroquinone and 1.5% of other compounds. The 70% MSA catalyst in water is added with a flow rate of 0.97 g/h. At the top of the distillation column, pure methyl acrylate comprising 0.1% of phenothiazine is sent as reflux with a flow rate of 330 g/h.

The reaction is carried out for 196 h at a temperature of 140° C. under these conditions, with the following operating parameters:
  the alcohol/upgradeable acrylic acid (sum of acrylic acid monomer, dimer and trimer) molar ratio is 1.3,
  the feed flow rate per unit of useful reaction volume is 0.3 T/h/m$^3$, the reflux/feed of the reactants flow rate ratio is 1.1,
the mean residence time of the residue in the reactor, calculated by the ratio of the volume of reactor occupied to the residue purge flow rate, is 116 h,
the concentration of MSA present in the reaction mixture is 4.5%, determined by measurement of the acidity,
the concentration of phenothiazine, measured by analysis, in the reactor is 0.05%.

The crude ester mixture condensed at the column top decants into 2 phases which are separated and separately analysed. Over a withdrawal period of 16 h, 9532 g of organic phase, composed of 3.2% of methanol, 5.15% of water and 0.26% of acrylic acid, the remainder being essentially methyl acrylate, and 458 g of aqueous phase, consisting of 13.1% of methanol; 7.33% of methyl acrylate and 0.06% of acrylic acid, the remainder being essentially composed of water, are obtained.

The reaction yield, determined by the molar ratio of methyl acrylate produced (subtraction made of the methyl acrylate fed via the reflux and the feed stream) relative to the upgradeable acrylic acid fed in (sum of acrylic acid monomer, dimer and trimer), is 95.2%. This yield is also the mean yield obtained during 1 week of operation.

The dynamic viscosity of the reaction residue, measured using a Brookfield CAP1000+ viscosimeter at a temperature of 100° C. is 150 cP.

Example 2

The reactor is operated in the same way as during Test 1, apart from the following changes:
reaction temperature: 143° C.,
alcohol/upgradeable acrylic acid (sum of acrylic acid monomer, dimer and trimer) molar ratio: 1.4,
MSA concentration: 3.3%,
mixture sent as reflux at the column top, consisting of methyl acrylate comprising 0.5% of methanol, 2.6% of methyl acetate and 2.4% of water, so as to take into consideration the recycling of a mixture resulting from the following stages of the process, comprising a few impurities.

Under these conditions debased by the recycling of impurities in the reflux mixture, which are kept constant for 200 h, the mean residence time of the residue in the reactor is 114 h and the mean reaction yield over a period of operation of 100 h reaches 97.8%.

The dynamic viscosity of the reaction residue, measured at a temperature of 100° C., is 160 cP, with a measured phenothiazine concentration of 0.05%.

Example 3 (Comparative)

The reactor is operated for 53 h in the same way as Test 1, with the following operational parameters:
composition of the acrylic acid of crude ester grade: 88.8% of acrylic acid monomer, 9% of acrylic acid dimer, 0.3% of acrylic acid trimer, 0.27% of phenothiazine and 0.19% of hydroquinone,
feed flow rate per unit of useful reaction volume is 0.3 T/h/m³,
alcohol/upgradeable acrylic acid (sum of acrylic acid monomer, dimer and trimer) molar ratio is 1.3,
reflux flow rate/feed flow rate of the reactants ratio is 1.1,
MSA concentration: 11%,
residence time of the residue greater than 300 h.
The reaction temperature is reduced to 128° C. and the viscosity of the residue, measured at 100° C., is 150 cP.

Despite the high concentration of catalyst deployed, the mean yield calculated during the operation is only 92.7%.

Example 4 (Comparative)

The reactor is operated for 47 h in the same way, with the same feed stream and under the same conditions as Test 3, apart from:
an alcohol/upgradeable acrylic acid (sum of acrylic acid monomer, dimer and trimer) molar ratio of 1.45,
an MSA concentration of 10%,
a reaction temperature of 135° C.

By virtue of the higher reaction temperature than that of Test 3, the mean yield calculated during the operation is 97%. On the other hand, the viscosity of the reaction mixture, measured at 100° C., is much greater than 250 cP (limit of measurement of the viscosimeter) making it very difficult to empty the reactor, and solids could be observed during this emptying operation. The concentration of phenothiazine measured in the reaction mixture is less than 10 ppm.

Example 5 (Comparative)

The reactor is operated for 62 h in the same way as during Test 1, with the following operational parameters:
composition of the acrylic acid of crude ester grade: 75.5% of acrylic acid monomer, 18.8% of acrylic acid dimer, 1% of acrylic acid trimer, 0.85% of phenothiazine and 0.42% of hydroquinone,
feed flow rate per unit of useful reaction volume is 0.3 T/h/m³,
alcohol/upgradeable acrylic acid (sum of the acrylic acid monomer, dimer and trimer) molar ratio is 1.3,
reflux flow rate/feed flow rate ratio is 1.1,
reaction temperature: 140° C.

The concentration of MSA in the reaction mixture is reduced to 2.2%.

The mean yield calculated during the operation reaches only 85.9%. Due to the low reactivity of the reaction, the purge flow rate for providing a constant level in the reactor is increased, and the residence time which results from these debased conditions is 34 h.

Example 6 (Comparative)

The reactor is operated for 46 h in the same way as during Test 1, with the following operational parameters:
composition of the acrylic acid of crude ester grade: 88.8% of acrylic acid monomer, 9% of acrylic acid dimer, 0.3% of acrylic acid trimer, 0.27% of phenothiazine and 0.19% of hydroquinone,
feed flow rate per unit of useful reaction of volume is 0.3 T/h/m³,
reflux flow rate/feed flow rate ratio is 1.1,
reaction temperature: 140° C.,
MSA concentration: 4%.
The alcohol/upgradeable acrylic acid (sum of acrylic acid monomer, dimer and trimer) molar ratio is reduced to 1.1.
The mean residence time of the residue in the reactor is 87 h and the mean yield calculated during the operation is only 87.5%.

The invention claimed is:
1. A method for continuous preparation of light acrylate selected from the group consisting of methyl acrylate and ethyl acrylate, by:

reacting a corresponding light alcohol selected from the group consisting of methanol and ethanol with a stream of acrylic acid of crude ester grade comprising Michael adducts at a content by weight above 8%, according to which the following are carried out simultaneously in a single reaction zone: thermal dissociation of the Michael adducts present in said stream of acrylic acid of crude ester grade, or generated in situ in the reaction zone, and the reaction of esterification, with a light alcohol, of the acrylic acid present in said stream of acrylic acid of crude ester grade and/or generated in situ by said thermal dissociation, submitting effluent leaving the reaction zone to a chain of treatment and purification providing a purified light acrylate, while withdrawing reaction residue using a pump, wherein an excess of light acrylate is maintained in the reaction zone by reflux of an essentially water-free light acrylate phase at a flow rate by mass maintained above 0.8, said flow rate expressed by mass relative to a feed flow rate by mass of reactants to said reaction zone.

2. Method according to claim 1 wherein the light acrylate is methyl acrylate.

3. Method according to claim 1 wherein the acrylic acid is from a production process using propylene as raw material.

4. Method according to claim 1 wherein the acrylic acid is from a production process using glycerol or glycerin as raw material, or from a process for the dehydration of lactic acid, of 3-hydroxy-propionic acid or of their ammonium salts.

5. Method according to claim 1 wherein the stream of acrylic acid of crude ester grade is obtained during purification of crude acrylic acid recovered by means of an adsorption column fed with a solvent at the outlet of the acrylic acid synthesis reactor.

6. Method according to claim 1 wherein the stream of acrylic acid of crude ester grade is obtained during purification of acrylic acid recovered by means of a dehydration column without using solvent for extraction or azeotropic distillation, at the outlet of the acrylic acid synthesis reactor.

7. Method according to claim 1 wherein the stream of acrylic acid of crude ester grade comprises the heavy fraction separated at the bottom of a last purification step called tailing in an acrylic acid synthesis process.

8. Method according to claim 1 wherein a light acrylate phase comprising less than 5% by weight of water is sent as reflux to the reaction zone with a flow rate by mass above 0.8 expressed relative to the feed flow rate by mass of the reactants.

9. Method according to claim 1 wherein dynamic viscosity of the reaction residue, measured at 100° C. with a Brookfield rotary viscosimeter, is less than 200 cP.

* * * * *